US009102590B2

(12) United States Patent
Kanou et al.

(10) Patent No.: US 9,102,590 B2
(45) Date of Patent: Aug. 11, 2015

(54) METHOD FOR PRODUCING ACRYLAMIDE AQUEOUS SOLUTION

(75) Inventors: Makoto Kanou, Yokohama (JP); Norifumi Hagiya, Yokohama (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 14/118,075

(22) PCT Filed: May 21, 2012

(86) PCT No.: PCT/JP2012/062934
§ 371 (c)(1),
(2), (4) Date: Nov. 15, 2013

(87) PCT Pub. No.: WO2012/157777
PCT Pub. Date: Nov. 22, 2012

(65) Prior Publication Data
US 2014/0106415 A1    Apr. 17, 2014

(30) Foreign Application Priority Data

May 19, 2011    (JP) .................................. 2011-112429

(51) Int. Cl.
*C12P 13/02*    (2006.01)
*C07C 231/06*    (2006.01)
*C07C 231/22*    (2006.01)

(52) U.S. Cl.
CPC ............. *C07C 231/06* (2013.01); *C07C 231/22* (2013.01); *C12P 13/02* (2013.01)

(58) Field of Classification Search
IPC .................................. C12P 13/02; C07C 231/06
See application file for complete search history.

(56) References Cited

U.S. PATENT DOCUMENTS

| 3,459,639 | A | 8/1969 | Marcel Borrel et al. |
|---|---|---|---|
| 4,248,968 | A | 2/1981 | Watanabe et al. |
| 4,343,899 | A * | 8/1982 | Watanabe et al. ............. 435/129 |
| 4,637,982 | A | 1/1987 | Yamada et al. |
| 5,200,331 | A * | 4/1993 | Kawakami et al. ........... 435/129 |
| 5,998,180 | A | 12/1999 | Armitage et al. |
| 6,162,624 | A | 12/2000 | Symes et al. |
| 6,361,981 | B1 | 3/2002 | Symes et al. |
| 2004/0048348 | A1 | 3/2004 | Murao et al. |
| 2008/0038788 | A1* | 2/2008 | Mistry et al. ................... 435/129 |
| 2011/0006258 | A1 | 1/2011 | Oda et al. |
| 2011/0021819 | A1 | 1/2011 | Kanou et al. |

FOREIGN PATENT DOCUMENTS

| EP | 2 264 003 A1 | 12/2010 |
|---|---|---|
| GB | 2076820 A * | 12/1981 |
| JP | 39 10109 | 6/1964 |
| JP | 40 7171 | 4/1965 |
| JP | 40 7172 | 4/1965 |
| JP | 41 1773 | 2/1966 |
| JP | 45 11284 | 4/1970 |
| JP | 62 91189 | 4/1987 |
| JP | 4 197189 | 7/1992 |
| JP | 2009 214099 | 9/2009 |
| JP | 2010 222309 | 10/2010 |
| WO | 97 21805 | 6/1997 |
| WO | 97 21827 | 6/1997 |
| WO | 02 50297 | 6/2002 |
| WO | 03 033716 | 4/2003 |
| WO | WO 03/066800 A2 | 8/2003 |
| WO | WO 03/066800 A3 | 8/2003 |
| WO | 2009 113617 | 9/2009 |
| WO | 2009 113654 | 9/2009 |
| WO | 2011 102510 | 8/2011 |
| WO | 2012 039407 | 3/2012 |

OTHER PUBLICATIONS

U.S. Appl. No. 14/117,754, filed Nov. 14, 2013, Kanou, et al.
International Search Report issued Aug. 28, 2012 in PCT/JP2012/062926.
INEOS Nitriles Acrylonitrile Specification Tests; Organic Impurities by Gas Chromatography, INEOS USA LLC, pp. 1-9, (retrieved on Aug. 14, 2012) Retrieved from the Internet: <URL: http:// www.Ineosnitriles.com/media/files/ACRN-28-5%20GC.pdf>.
Chavez, S.L., et al., "Photoinitiated Polymerization of Acrylamide and Methacrylamide", Chem. Eng. Commun., vol. 24, pp. 21-36, (1983).
Ikeda, Y., et al., "Hydrogen transfer polymerization of acrylamide derivatives by sodium naphthalene", Japanese Journal of Polymer Science and Technology, vol. 44, No. 6, pp. 451-460, (Jun. 1987) (with partial English translation), Abstract only.
International Search Report Issued Jun. 26, 2012 in PCT/JP12/062934 Filed May 21, 2012.
Extended European Search Report issued Oct. 22, 2014 in Patent Application No. 12785713.4.
Jonathan Hughes, et al., "Application of whole cell rhodococcal biocatalysts in acrylic polymer manufacture", Antonie van Leeuwenhoek, vol. 74, XP002936324, Jan. 1, 1998, pp. 107-118.

* cited by examiner

*Primary Examiner* — Rosanne Kosson
(74) *Attorney, Agent, or Firm* — Oblon, McClelland, Maier & Neustadt, L.L.P.

(57) ABSTRACT

There is provided a method for producing an aqueous acrylamide solution by producing acrylamide by reacting a composition including acrylonitrile with water, in which the composition including acrylonitrile includes 20 to 80 mg of methacrylonitrile per 1 kg of the total weight of the composition including acrylonitrile. According to the present invention, a production method allowing stable obtainment of an aqueous acrylamide solution can be provided as polymerization of the acrylamide can be suppressed without causing a decreas+455e in quality.

13 Claims, No Drawings

METHOD FOR PRODUCING ACRYLAMIDE AQUEOUS SOLUTION

TECHNICAL FIELD

The present invention relates to a method for producing an aqueous acrylamide solution.

The present application claims priority to Japanese Patent Application No. 2011-112429, which has been filed in Japan on May 19, 2011, which is hereby incorporated by reference in its entirety.

BACKGROUND ART

Acrylamide has many applications, such as flocculating agents, petroleum recovering agents, paper strength enhancers in the paper producing industry, and thickeners for papermaking, and is a useful substance as a raw material for polymers.

Among industrial processes for acrylamide production, used long time ago is a sulfuric acid hydrolysis process which consists of the step of heating acrylonitrile together with sulfuric acid and water to obtain an aqueous solution of acrylamide sulfate salts. This process has then been replaced with a copper-catalyzed process in which acrylonitrile is reacted with water in the presence of a copper catalyst (for example, metal copper, reduced copper, Raney copper, or the like) to obtain an aqueous solution of acrylamide. In addition, in recent years, as a production process with fewer by-products, industrial production based on a biocatalyst method is also carried out as a biocatalyst method for obtaining an aqueous solution of acrylamide by using a biocatalyst such as nitrile hydratase derived from microorganisms (for example, Patent Documents 1 to 4).

As in the case of many unsaturated monomers, acrylamide is easy to polymerize by the action of light or heat and also has a property of very easily polymerizing particularly upon contact with the surface of iron, so that an aqueous solution of acrylamide has been difficult to stably handle since the polymerization of acrylamide easily occurs during each step of its production or during its preservation.

A method of using various stabilizers has been proposed as a method for stabilization by suppressing polymerization of acrylamide. Examples of the stabilizers include thiourea, ammonium rhodanide, nitrobenzol (Patent Document 5), ferron (Patent Document 6), furil dioxime (Patent Document 7), cyanide complex compound of chromium (Patent Document 8), p-nitrosodiphenyl hydroxyamine (Patent Document 9), and so on. Those stabilizers are used for preventing polymerization during a process of producing acrylamide or for stabilization of an aqueous solution of acrylamide.

CITATION LIST

Patent Document

Patent Document 1: JP 56-17918 B
Patent Document 2: JP 59-37951 B
Patent Document 3: JP 02-470 A
Patent Document 4: WO 2009/113654 A
Patent Document 5: JP 39-10109 B
Patent Document 6: JP 40-7171 B
Patent Document 7: JP 40-7172 B
Patent Document 8: JP 41-1773 B
Patent Document 9: JP 45-11284 B

DISCLOSURE OF THE INVENTION

Problem to be Solved by the Invention

The stabilizers described above all correspond to polymerization inhibitors. Stabilizers with a small stabilizing effect, that is, polymerization inhibiting effect, have problems of reduced quality of acrylamide, such as discoloration and reduced purity of acrylamide, because they should be added in large amounts to acrylamide. On the other hand, stabilizers with a high polymerization inhibiting effect may adversely affect the polymerization operations during production of acrylamide polymers such as having a difficulty to obtain desired high molecular weight polymers or reduced polymerization rate, even when used in small amounts.

The present invention is devised in view of the above circumstances, and an object of the present invention is to provide a production method with which it is possible to suppress acrylamide polymerization without lowering quality and thereby obtain a stable aqueous acrylamide solution.

BRIEF SUMMARY OF THE INVENTION

As a result of intensive studies to solve the problems stated above, the inventors of the present invention have found that when acrylamide is produced from acrylonitrile containing a predetermined amount of methacrylonitrile, polymerization of acrylamide during its production and preservation can be suppressed without lowering the quality of acrylamide to thereby significantly improve its stability, and the present invention is completed accordingly.

The present invention has following aspects.

[1] A method for producing an aqueous acrylamide solution by reacting acrylonitrile with water to produce acrylamide, in which acrylonitrile containing 20 to 80 mg/kg of methacrylonitrile is used as the acrylonitrile,

[2] The method for producing an aqueous acrylamide solution described in [1], in which the reaction with water is performed in the presence of a biocatalyst,

[3] The method for producing an aqueous acrylamide solution described in [1] or [2], in which the acrylonitrile also contains 2 to 20 mg/kg of acetonitrile, and

[4] The method for producing an aqueous acrylamide solution described in any one of [1] to [3], in which the concentration of the acrylamide in the aqueous acrylamide solution is 30 to 60% by mass.

DETAILED DESCRIPTION OF THE INVENTION

Specifically, the present invention relates to the followings.

(1) A method for producing an aqueous acrylamide solution including reacting a composition containing acrylonitrile with water to produce acrylamide, in which the composition containing acrylonitrile contains 20 to 80 mg of methacrylonitrile per 1 kg of the total weight of the composition containing acrylonitrile, (2) The method for producing an aqueous acrylamide solution described in (1), in which the method includes performing the reaction of the composition containing acrylonitrile with water in the presence of a biocatalyst, (3) The method for producing an aqueous acrylamide solution described in (1) or (2), in which the composition containing acrylonitrile also contains 2 to 20 mg/kg of acetonitrile per 1 kg of the total weight of the composition containing acrylonitrile, and (4) The method for producing an aqueous acrylamide solution described in any one of (1) to (3), in which the concentration of the acrylamide in the aqueous acrylamide solution is 30 to 60% by mass relative to the total mass of the aqueous acrylamide solution.

Effect of the Invention

According to the production method of the present invention, a stable aqueous acrylamide solution is obtained as polymerization of acrylamide can be suppressed without lowering the quality.

BEST MODE(S) FOR CARRYING OUT THE INVENTION

Hereinafter, embodiments of the present invention will be described. The following embodiments are merely examples provided for illustrating the present invention, and the present invention is not intended to be limited thereto. The present invention may be carried out in various embodiments without departing from the spirit of the present invention.

All publications cited in this specification, including technical literatures, patent laid-open publications, patent publications and other patent documents, are incorporated herein by reference in their entirety.

The present invention relates to a method for producing an aqueous acrylamide solution by reacting acrylonitrile with water to produce acrylamide. Examples of the method of reacting acrylonitrile with water include a sulfuric acid hydration process which is the process for earlier industrial production of acrylamide, a copper-catalyzed process which is a current major process for industrial production, and a biocatalyst process which is recently industrialized, and any method can be used. By using specific acrylonitrile for the reaction with water, a stabilizing effect of suppressing polymerization of acrylamide to be produced can be obtained with any method. Further, the aqueous acrylamide solution to be obtained has favorable quality, and therefore a negative influence on a polymerization process for producing an acrylamide polymer is also not exhibited.

The composition containing acrylonitrile that is used in the present invention is a mixture of acrylonitrile and methacrylonitrile; or a mixture of acrylonitrile, methacrylonitrile, and acetonitrile.

The composition containing acrylonitrile that is used in the present invention contains 20 to 80 mg, and preferably 30 to 60 mg of methacrylonitrile per 1 kg of the total weight of the composition containing acrylonitrile. When acrylamide is produced by reacting a composition containing acrylonitrile in which methacrylonitrile content is less than 20 mg per 1 kg of the total weight of the composition containing acrylonitrile with water, the stabilizing effect of suppressing polymerization of acrylamide is hardly obtained. On the other hand, when the methacrylonitrile content is more than 80 mg per 1 kg of the total weight of the composition containing acrylonitrile, the stabilizing effect is lowered.

In acrylonitrile as a raw material (that is, the composition containing acrylonitrile according to the present invention), methacrylonitrile is generally present as impurities.

When the methacrylonitrile content in acrylonitrile as a raw material (for example, commercially available acrylonitrile or acrylonitrile synthesized by a method known in the field) has a desired value, the raw material can be directly used for the reaction with water.

When the methacrylonitrile content in acrylonitrile as a raw material is lower than a desired value, it is possible to add methacrylonitrile to the raw material to have a desired value. As for the methacrylonitrile to be added, commercially available methacrylonitrile may be used or methacrylonitrile synthesized by a method known in the field may be used. When the addition amount of methacrylonitrile is extremely tiny amount relative to acrylonitrile, a diluted methacrylonitrile liquid may be also added for easy addition. At that time, as for the liquid for dilution, water may be used. However, when a decrease in the concentration of acrylonitrile caused by addition of diluted methacrylonitrile liquid is not desirable, it is possible that methacrylonitrile is diluted in acrylonitrile at a desired concentration and the diluted liquid is added to acrylonitrile.

When the methacrylonitrile content in acrylonitrile as a raw material is higher than a desired value, methacrylonitrile can be removed by purification of the raw material. Examples of the purification method for removing methacrylonitrile in a composition containing acrylonitrile include rectification. Rectification of the composition containing acrylonitrile can be carried out by a known method, for example, by a method described in JP 2010-222309 A.

Adjustment of the methacrylonitrile content in the composition containing acrylonitrile may be also carried out by mixing a composition containing acrylonitrile which contains methacrylonitrile at high content (for example, higher than 80 mg/kg) and a composition containing acrylonitrile which contains methacrylonitrile at low content (for example, lower than 20 mg/kg). By adjusting the methacrylonitrile content in each composition containing acrylonitrile, their mixing ratio, or the like, desired methacrylonitrile content can be obtained.

It is preferable that the composition containing acrylonitrile that is used in the present invention also contain 2 to 20 mg, and preferably 5 to 15 mg of acetonitrile per 1 kg of the total weight of the composition containing acrylonitrile. When acrylamide is produced by reacting a composition containing acrylonitrile in which acetonitrile content is at least 2 mg per 1 kg of the total weight of the composition containing acrylonitrile with water, the stabilizing effect of suppressing polymerization of acrylamide is enhanced. On the other hand, when the acetonitrile content is more than 20 mg per 1 kg of the total weight of the composition containing acrylonitrile, the stabilizing effect may be lowered.

Similar to methacrylonitrile, acetonitrile is generally present as impurities in acrylonitrile as a raw material (that is, the composition containing acrylonitrile according to the present invention).

Adjustment of the acetonitrile content in the composition containing acrylonitrile may be carried out in the same manner as methacrylonitrile.

Each of the methacrylonitrile content and the acetonitrile content in the composition containing acrylonitrile can be measured by gas chromatography mass analysis, liquid chromatography mass analysis, or the like.

As for the method of reacting acrylamide with water in the present invention, a biocatalyst method is preferable in that acrylamide with high purity can be obtained with fewer reaction by-products.

The biocatalyst method is a method of producing acrylamide by reacting acrylonitrile with water in the presence of a biocatalyst, and it is described in many literatures, for example, JP 56-17918 B, JP 59-37951 B, JP 02-470 A, and WO 2009/113654 A. In the present invention, except that a specific acrylonitrile is used for the reaction with water, a known method can be used.

Herein, the biocatalyst includes animal cells, plant cells, cell organelles, or cell bodies of microorganisms (cell bodies of living or dead microorganisms); or treated products thereof, which contain an enzyme catalyzing a desired reaction (that is, nitrile hydratase).

Such treated products include an enzyme (that is, crude or purified enzyme) extracted from the animal cells, plant cells, cell organelles, cell bodies of microorganisms; or animal cells, plant cells, cell organelles, cell bodies of microorganisms, or enzymes themselves which are immobilized on a carrier; or the like.

Examples of the method for immobilization include entrapping, cross-linking, and carrier binding. Entrapping refers to a technique by which cell bodies of microorganisms or enzymes are enclosed within a fine lattice of polymer gel or coated with a semipermeable polymer membrane. Cross-linking refers to a technique by which enzymes are cross-linked with a reagent having two or more functional groups (that is, a multifunctional cross-linking agent). Furthermore, carrier binding refers to a technique by which enzymes are bound to a water insoluble carrier.

Examples of a carrier (that is, an immobilization carrier) for use in immobilization include glass beads, silica gel, polyurethane, polyacrylamide, polyvinyl alcohol, carrageenan, alginic acid, agar and gelatin.

Cell bodies of microorganisms or treated products thereof are particularly preferable as a biocatalyst.

Examples of the above microorganisms include microorganisms belonging to the genus *Nocardia*, genus *Corynebacterium*, genus *Bacillus*, genus *Pseudomonas*, genus *Micrococcus*, genus *Rhodococcus*, genus *Acinetobacter*, genus *Xanthobacter*, genus *Streptomyces*, genus *Rhizobium*, genus *Klebsiella*, genus *Enterobacter*, genus *Erwinia*, genus *Aeromonas*, genus *Citrobacter*, genus *Achromobacter*, genus *Agrobacterium* and genus *Pseudonocardia*, or the like.

Production of an aqueous acrylamide solution using a biocatalyst may be carried out by continuous reaction, by which acrylamide is produced in a continuous manner, or by batch reaction, by which acrylamide is produced in a non-continuous manner. Although not limited thereto, it is preferably carried out by continuous reaction.

When a continuous reaction is carried out, an aqueous acrylamide solution is produced in a continuous manner without collecting the entire reaction mixture in the reactor while maintaining continuous or intermittent supply of raw materials for reaction (containing a biocatalyst, water as a raw material, and acrylonitrile) to the reactor and continuous or intermittent recovery of the reaction mixture (containing the produced acrylamide) from the reactor.

When a batch reaction is carried out, an aqueous acrylamide solution is produced by reaction after supplying an entire amount of the raw materials for reaction to the reactor or by reaction with continuous or intermittent supply of remaining part of the raw materials for reaction to the reactor after injecting part of the raw materials for reaction to the reactor.

As for the type of the reactors, reactors of various types such as stirring tank type, fixed bed type, fluid bed type, moving bed type, tubular type, or tower type may be used. It is possible that only one reactor is used or plural reactors are used in combination. When plural reactors are used in combination, concentration of the recovered acrylamide in a reaction mixture is higher at a downstream side. For such reasons, based on the number of the reactors, concentration of acrylamide in an aqueous acrylamide solution that is finally obtained can be controlled.

When continuously performing a reaction using plural reactors, the reactor into which the biocatalyst and acrylonitrile are to be supplied is not limited to the most upstream reactor, and the materials may also be introduced into a reactor downstream thereof, as long as it is within a range in which efficiency of the reaction or the like are not impaired too much.

Among the raw materials for reaction, water as a raw material is used for the reaction of acrylonitrile with water for producing acrylamide. Examples of the water as a raw material include water; or an aqueous solution containing acids or salts that are dissolved in water. Examples of the acids include phosphoric acid, acetic acid, citric acid, and boric acid. Examples of the salts include sodium slat, potassium salt, and ammonium salt of the acids. Specific examples of the water as a raw material include, although not particularly limited thereto, pure water, tap water, tris buffer solution, phosphate buffer solution, acetate buffer solution, citrate buffer solution, and borate buffer solution. pH of the water as a raw material is preferably between 5 and 9 (25° C.).

Although the use amount of the biocatalyst may vary depending on the type and form of the biocatalyst to be used, it is preferably adjusted such that the activity of the biocatalyst to be introduced into a reactor is around 50 to 500 U per mg of dried cell bodies of microorganisms at a reaction temperature of 10° C. The above unit "U (unit)" is intended to mean that one micromole of acrylamide is produced for one minute from acrylonitrile, which is measured by using acrylonitrile to be used for production.

Although the use amount of the composition containing acrylonitrile may vary depending on the type and form of the biocatalyst to be used, it is preferably adjusted such that the acrylonitrile concentration in the raw materials for reaction is around 0.5% to 15.0% by mass with respect to the raw materials for reaction.

The reaction temperature (that is, temperature of the reaction mixture) is, although not particularly limited, preferably 10 to 50° C., and more preferably 20 to 40° C. When the reaction temperature is at least 10° C., reaction activity of the biocatalyst can be sufficiently increased. Further, when the reaction temperature is 40° C. or lower, deactivation of the biocatalyst can be easily suppressed.

The reaction time is, although not particularly limited, preferably 1 to 50 hours, and more preferably 3 to 30 hours.

When production of the aqueous acrylamide solution is carried out by continuous reaction, fluid rate at the time of collecting the reaction mixture from the reactor is determined based on addition rate of acrylonitrile and the biocatalyst such that the production can be made in a continuous manner without collecting the entire reaction mixture in the reactor.

For the purpose of facilitating stabilization, at least one water soluble monocarboxylic acid salt containing two or more carbon atoms may be added to the raw materials for the reaction used for the reaction of acrylonitrile with water or to the reaction mixture during or after the reaction with water.

The water soluble monocarboxylic acid salt may be any one of a salt of a saturated monocarboxylic acid or a salt of an unsaturated monocarboxylic acid. Examples of the saturated carboxylic acid include acetic acid, propionic acid, and n-caproic acid. Examples of the unsaturated carboxylic acid include acrylic acid, methacrylic acid, and vinyl acetic acid. Typical salts are sodium salts, potassium salts, and ammonium salts.

Addition amount of the water soluble monocarboxylic acid is preferably an amount which is 20 to 5000 mg/kg as an acid relative to acrylamide in the reaction mixture (aqueous acrylamide solution) that is finally obtained.

In the present invention, acrylamide concentration in the aqueous acrylamide solution is preferably 30 to 60% by mass, more preferably 35 to 55% by mass, and still more preferably 40 to 50% by mass relative to the total weight of the aqueous acrylamide solution.

If the acrylamide concentration is higher than 60% by mass, crystals of acrylamide may easily precipitate near ambient temperature and hence a heating apparatus is required, so that not only facility costs will be increased, but also temperature control and other operations will be complicated. For such reasons, the concentration of the aqueous acrylamide solution of the present invention is, for example, preferably 60% by mass or less, more preferably 55% by mass or less, and most preferably 50% by mass or less, although it is not particularly limited as long as it is within the range where crystals of acrylamide will not precipitate even near ambient temperature.

Meanwhile, if the acrylamide concentration is lower than 30% by mass, it is economically disadvantageous from the industrial standpoint because the tank volume used for storage or keeping will be excessively large or transport costs will also be increased. Thus, the acrylamide concentration in the aqueous acrylamide solution is, for example, preferably 30% by mass or more, more preferably 35% by mass or more, and most preferably 40% by mass or more.

The acrylamide concentration in the aqueous acrylamide solution can be adjusted by concentration of acrylonitrile in the raw materials for the reaction, type or shape of the biocatalyst to be used, or the reaction condition (that is, reaction temperature, reaction time, or number of the reactor) or the like.

It is believed that, in the aqueous acrylamide solution obtained by reacting acrylonitrile containing a predetermined amount of methacrylonitrile with water, methacrylonitrile or its reaction product with water is contained. However, there is almost no bad influence on the polymerization (for example, difficulty in obtaining a polymer with desired high molecular weight, decreased polymerization rate, or the like). Thus, the aqueous acrylamide solution obtained by the production method of the present invention can be directly subjected, depending on the use thereafter, to a polymerization process to obtain a desired acrylamide polymer.

The present invention will be further described in more detail by way of the following examples, but the present invention is not limited to them.

In each example described below, "%" represents "% by mass", unless specifically described otherwise.

As for the pH, values at 25° C. were measured by a glass electrode method.

EXAMPLE 1

(Preparation of Biocatalyst)
*Rhodococcus rhodochrous* J1 strain having nitrile hydratase activity (Accession number: PERM BP-1478; internationally deposited to International Patent Organism Depositary, National Institute of Advanced Industrial Science and Technology (Chuo 6, Higashi 1-1-1, Tsukuba-shi, Ibaraki, Japan) on Sep. 18, 1987) was aerobically cultured in a medium containing 2% glucose, 1% urea, 0.5% peptone, 0.3% yeast extract and 0.05% cobalt chloride (pH 7.0) at 30° C. Using a centrifuge and 50 mM phosphate buffer (pH 7.0), the obtained culture was subjected to harvest and washing, thereby preparing a bacterial cell suspension as a biocatalyst (dried cell bodies: 15% by mass).

(Adjustment of Methacrylonitrile Concentration)
Methacrylonitrile concentration and acetonitrile concentration in acrylonitrile (hereinbelow, "acrylonitrile A") manufactured by Dia-Nitrix Co., Ltd. were analyzed by gas chromatography (column: fused silica capillary No. 55 DB-225, column length: 25 m, oven temperature: temperature was increased from 50° C. to 200° C., detector temperature: 250° C., carrier gas: helium, split ratio: 1/50, detector: FID, and injection amount: 0.6 μL). As a result, in the acrylonitrile A, methacrylonitrile concentration was 12 mg/kg and acetonitrile concentration was 1 mg/kg.

By adding 1.02 g of methacrylonitrile (manufactured by Kanto Chemical Co., Inc., purity of 98%) to 99 g of acrylonitrile A, 1% diluted methacrylonitrile liquid was prepared. Next, by adding 0.20 g of the 1% diluted methacrylonitrile liquid to 100 g of the acrylonitrile A, acrylonitrile in which methacrylonitrile concentration was 20 mg/kg and acetonitrile concentration was 1 mg/kg was obtained (hereinbelow, "acrylonitrile B").

(Reaction from Acrylonitrile to Acrylamide)
With the following method, acrylonitrile B was reacted with water to obtain an aqueous acrylamide solution.

Reactors equipped with a jacket having internal volume of 1 L (internal diameter of 10 cm) were connected in series to have seven tanks. To the first tank, 50 mM phosphate buffer solution (pH 7) was added at 780 mL/hr, the acrylonitrile B was added at 175 mL/hr, and suspension of the cell bodies were added at 2.0 g/hr in a continuous manner. To the second tank, only the acrylonitrile B was added at 175 mL/hr in a continuous manner. To the third tank, only the acrylonitrile B was added at 146 mL/hr in a continuous manner, and to the fourth tank, only the acrylonitrile B was added at 88 mL/hr in a continuous manner. Each tank was all subjected to stirring. The reaction temperature was controlled by using jacket cooling water (10° C.) such that the liquid temperature of the first tank to the seventh tank becomes 21, 22, 23, 23, 24, 25, and 25° C., respectively.

One day later, the reaction liquid discharged from the seventh tank was analyzed by gas chromatography (column: manufactured by Waters, PoraPak-PS, 1 m, 180° C., carrier gas: helium, detector: FID). As a result, only acrylamide was detected and non-reacted acrylonitrile was not detected. Acrylamide concentration in the reaction liquid was 50%.

(Evaluation of Stability of Aqueous Acrylamide Solution)
The aqueous acrylamide solution was taken in an amount of 30 g and introduced into a 50 mL polypropylene container (a product of AS ONE Corporation, under the trade name of Ai-Boy wide-mouth bottle).

A stainless washer (SUS304, inner diameter: 9 mm, outer diameter: 18 mm) was washed with acetone and then with pure water, followed by drying. After drying, the washer was introduced into the 50 mL polypropylene container containing the aqueous acrylamide solution. This polypropylene container was held in a thermostat kept at 70° C. to measure the number of days required until the acrylamide in the aqueous acrylamide solution is polymerized (that is, until a pop corn-like polymerized product was produced).

As a result, the pop corn-like polymerized product was produced after 19 days.

EXAMPLE 2

By adding 0.685 g of 1% diluted methacrylonitrile liquid which has been prepared in Example 1 to 100 g of the acrylonitrile A, acrylonitrile in which methacrylonitrile concentration is 80 mg/kg and acetonitrile concentration is 1 mg/kg was obtained (hereinbelow, "acrylonitrile C"). The acrylonitrile C was reacted with water in the same order as Example 1 to obtain an aqueous acrylamide solution.

Stability of the obtained aqueous acrylamide solution was evaluated in the same order as Example 1. As a result, a pop corn-like polymerized product was produced after 22 days.

EXAMPLE 3

By adding 0.01 g of acetonitrile (manufactured by Kanto Chemical Co., Inc., purity of 99%) to 99.9 g of acrylonitrile B, 0.01% diluted acetonitrile liquid was prepared. Next, by adding 1.02 g of the 0.01% diluted acetonitrile liquid to 100 g of the acrylonitrile B, acrylonitrile in which methacrylonitrile concentration was 20 mg/kg and acetonitrile concentration was 2 mg/kg was obtained (hereinbelow, "acrylonitrile D"). The acrylonitrile D was reacted with water in the same order as Example 1 to obtain an aqueous acrylamide solution.

Stability of the obtained aqueous acrylamide solution was evaluated in the same order as Example 1. As a result, a pop corn-like polymerized product was produced after 33 days.

EXAMPLE 4

By adding 0.2 g of acetonitrile (manufactured by Kanto Chemical Co., Inc., purity of 99%) to 99 g of acrylonitrile B, 0.2% diluted acetonitrile liquid was prepared. Next, by adding 0.96 g of the 0.2% diluted acetonitrile liquid to 100 g of the acrylonitrile B, acrylonitrile in which methacrylonitrile concentration was 20 mg/kg and acetonitrile concentration was 20 mg/kg was obtained (hereinbelow, "acrylonitrile E"). The acrylonitrile E was reacted with water in the same order as Example 1 to obtain an aqueous acrylamide solution.

Stability of the obtained aqueous acrylamide solution was evaluated in the same order as Example 1. As a result, a pop corn-like polymerized product was produced after 34 days.

EXAMPLE 5

By adding 1.47 g of the 0.2% diluted acetonitrile liquid prepared in Example 4 to 100 g of the acrylonitrile B, acrylonitrile in which methacrylonitrile concentration was 20 mg/kg and acetonitrile concentration was 30 mg/kg was obtained (hereinbelow, "acrylonitrile F"). The acrylonitrile F was reacted with water in the same order as Example 1 to obtain an aqueous acrylamide solution.

Stability of the obtained aqueous acrylamide solution was evaluated in the same order as Example 1. As a result, a pop corn-like polymerized product was produced after 18 days.

COMPARATIVE EXAMPLE 1

The acrylonitrile A was reacted with water in the same order as Example 1 to obtain an aqueous acrylamide solution.

Stability of the obtained aqueous acrylamide solution was evaluated in the same order as Example 1. As a result, a pop corn-like polymerized product was produced after 4 days.

COMPARATIVE EXAMPLE 2

By adding 0.889 g of the 1% diluted methacrylonitrile liquid prepared in Example 1 to 100 g of the acrylonitrile A, acrylonitrile in which methacrylonitrile concentration was 100 mg/kg and acetonitrile concentration was 1 mg/kg was obtained (hereinbelow, "acrylonitrile G"). The acrylonitrile G was reacted with water in the same order as Example 1 to obtain an aqueous acrylamide solution.

Stability of the obtained aqueous acrylamide solution was evaluated in the same order as Example 1. As a result, a pop corn-like polymerized product was produced after 7 days.

TABLE 1

|  | Methacrylonitrile concentration in acrylonitrile [mg/kg] | Acetonitrile concentration in acrylonitrile [mg/kg] | Number of days required for polymerization of acrylamide [Days] |
| --- | --- | --- | --- |
| Example 1 | 20 | 1 | 19 |
| Example 2 | 80 | 1 | 22 |
| Example 3 | 20 | 2 | 33 |
| Example 4 | 20 | 20 | 34 |
| Example 5 | 20 | 30 | 18 |
| Comparative example 1 | 12 | 1 | 4 |
| Comparative example 2 | 100 | 1 | 7 |

As described in the above results, by reacting acrylonitrile containing 20 to 80 mg/kg of methacrylonitrile, polymerization of the acrylamide can be suppressed during storage so that the stability of the aqueous acrylamide solution can be significantly improved.

In addition, as a result of evaluating the appearance of the aqueous acrylamide solution (that is, presence or absence of coloration), the polymerization rate at the time of producing an acrylamide polymer, and the molecular weight of the obtained acrylamide polymer or the like, favorable results were obtained from all of them, and no reduction in quality of the aqueous acrylamide solution was exhibited.

INDUSTRIAL APPLICABILITY

According to the present invention, an aqueous acrylamide solution can be conveniently stabilized without lowering quality of acrylamide. Therefore, the present invention is useful as a method for preventing polymerization of acrylamide during production, storage and/or transport of the aqueous acrylamide solution.

The invention claimed is:

1. A method for producing an aqueous acrylamide solution, the method comprising reacting an acrylonitrile composition and water in the presence of a catalyst to produce said aqueous acrylamide solution,
    wherein the acrylonitrile composition comprises acrylonitrile and 20 to 80 mg of methacrylonitrile per 1 kg of the acrylonitrile composition.

2. The method according to claim 1, wherein the reacting of the acrylonitrile composition and water is performed in the presence of a biocatalyst.

3. The method according to claim 1, wherein the acrylonitrile composition further comprises 2 to 20 mg of acetonitrile per 1 kg of the acrylonitrile composition.

4. The method according to claim 1, wherein the concentration of the acrylamide in the aqueous acrylamide solution is from 30 to 60% by mass relative to the total mass of the aqueous acrylamide solution.

5. The method according to claim 1, wherein the acrylonitrile composition comprises acrylonitrile and 30 to 60 mg of methacrylonitrile per 1 kg of the acrylonitrile composition.

6. The method according to claim 1, wherein the acrylonitrile composition further comprises 5 to 15 mg of acetonitrile per 1 kg of the acrylonitrile composition.

7. The method according to claim 5, wherein the acrylonitrile composition further comprises 5 to 15 mg of acetonitrile per 1 kg of the acrylonitrile composition.

8. The method according to claim 1, wherein the concentration of the acrylamide in the aqueous acrylamide solution is from 40 to 50% by mass relative to the total mass of the aqueous acrylamide solution.

9. The method according to claim 7, wherein the concentration of the acrylamide in the aqueous acrylamide solution is from 40 to 50% by mass relative to the total mass of the aqueous acrylamide solution.

10. The method according to claim 1, wherein said reacting of said acrylonitrile composition and water is conducted in the presence of said catalyst and a water soluble monocarboxylic acid salt containing two or more carbon atoms.

11. The method according to claim 10, wherein said water soluble monocarboxylic acid salt containing two or more carbon atoms is at least one selected from the sodium, potassium and ammonium salts of acetic acid, propionic acid, n-caproic acid, acrylic acid, methacrylic acid and vinyl acetic acid.

12. The method according to claim 1, wherein after said reacting of said acrylonitrile composition and water in the presence of a catalyst a water soluble monocarboxylic acid salt containing two or more carbon atoms is added to the aqueous acrylamide solution.

13. The method according to claim 12, wherein said water soluble monocarboxylic acid salt containing two or more carbon atoms is at least one selected from the group consisting of sodium, potassium and ammonium salts of acetic acid, propionic acid, n-caproic acid, acrylic acid, methacrylic acid and vinyl acetic acid.

* * * * *